(12) United States Patent
Watanabe et al.

(10) Patent No.: US 7,923,025 B2
(45) Date of Patent: Apr. 12, 2011

(54) PHARMACEUTICAL COMPOSITION FOR ORAL USE WITH IMPROVED ABSORPTION

(75) Inventors: Shunsuke Watanabe, Fujieda (JP); Kiyo Nakanishi, Yaizu (JP); Shigeo Takemura, Fujietda (JP); Yuuki Tsutsui, Shizuoka (JP)

(73) Assignee: Astellas Pharma Inc. (JP)

( * ) Notice: Subject to any disclaimer, the term of this patent is extended or adjusted under 35 U.S.C. 154(b) by 1467 days.

(21) Appl. No.: 10/345,051

(22) Filed: Jan. 15, 2003

(65) Prior Publication Data

US 2003/0175351 A1    Sep. 18, 2003

(51) Int. Cl.
*A61K 9/46* (2006.01)
*A61K 9/20* (2006.01)
(52) U.S. Cl. .................................... 424/451; 424/464
(58) Field of Classification Search ............... 424/78.08, 424/434
See application file for complete search history.

(56) References Cited

U.S. PATENT DOCUMENTS

| | | | |
|---|---|---|---|
| 4,537,772 A | 8/1985 | Alexander et al. | |
| 5,350,741 A | 9/1994 | Takada | |
| 5,445,830 A | 8/1995 | Ishizue et al. | |
| 5,726,154 A * | 3/1998 | Baudys et al. | 514/12 |
| 5,766,620 A | 6/1998 | Heiber et al. | |
| 5,849,322 A | 12/1998 | Ebert et al. | |
| 6,004,575 A | 12/1999 | Luessen et al. | |
| 6,368,635 B1 * | 4/2002 | Akiyama et al. | 424/501 |
| 6,458,383 B2 * | 10/2002 | Chen et al. | 424/451 |
| 7,008,640 B2 | 3/2006 | Watanabe et al. | |
| 2002/0150624 A1 | 10/2002 | Watanabe et al. | |
| 2005/0112206 A1 | 5/2005 | Watanabe et al. | |

FOREIGN PATENT DOCUMENTS

| | | | |
|---|---|---|---|
| EP | 0759303 A1 | | 2/1997 |
| EP | 1093818 | * | 1/1999 |
| EP | 1 093 818 A1 | | 4/2001 |

(Continued)

OTHER PUBLICATIONS

Asada et al., "Absorption Characteristics of Chemically Modified-Insulin Derivatives with Various Fatty Acids in the Small and Large Intestine," *Journal of Pharmaceutical Sciences*, Jun. 1995, pp. 682-687, vol. 84, No. 6.

(Continued)

*Primary Examiner* — Carlos A Azpuru
(74) *Attorney, Agent, or Firm* — Kilpatrick Townsend & Stockton LLP (57) ABSTRACT

The present invention relates to an agent for inhibiting decomposition of a biologically active peptide by a digestive enzyme, which is aminoalkyl methacrylate copolymer E as an effective ingredient, and an agent for reducing viscosity of the gastrointestinal mucosa and mucous layers distributed over this mucosa. The present invention relates to a method for inhibiting decomposition of a biologically active peptide by a digestive enzyme, or a method for reducing viscosity of the gastrointestinal mucosa and/or mucous layers distributed over the mucosa, by administration of aminoalkyl methacrylate copolymer E. Furthermore, the present invention relates to a pharmaceutical composition for oral use with improved absorption, which comprises a biologically active peptide and aminoalkyl methacrylate copolymer E. Excellent oral absorption of a biologically active peptide that were considered difficult to absorb by oral administration in the past, can be realized based on the ability to inhibit decomposition of a biologically active peptide, the ability to reduce viscosity of the gastrointestinal mucosa and/or mucous layers distributed over this mucosa, and the ability to improve permeability of a biologically active peptide in the gastrointestinal mucosa and/or mucous layers of the pharmaceutical composition of the present invention.

15 Claims, 3 Drawing Sheets

FOREIGN PATENT DOCUMENTS

| EP | 1093818 A1 | 4/2001 |
| EP | 1273306 A1 | 1/2003 |
| JP | 7138182 | 5/1995 |
| JP | 9278670 | 10/1997 |
| WO | WO 90/01329 | 2/1990 |
| WO | WO 96/06635 A1 | 3/1996 |
| WO | WO 00/02574 A1 | 1/2000 |
| WO | WO 00/43041 A1 | 7/2000 |
| WO | WO 02/05786 A1 | 1/2002 |

OTHER PUBLICATIONS

Hochman et al., "Mechanisms of Absorption Enhancement and Tight Junction Regulation," *Journal of Controlled Release*, 1994, pp. 253-267, vol. 29.

Kotzé et al., "Chitosans for Enhanced Delivery of Therapeutic Peptides Across Intestinal Epithelia: In Vitro Evaluation in Caco-2 Cell Monolayers," *International Journal of Pharmaceutics*, 1997, pp. 243-253, vol. 159.

Luessen et al., "Mucoadhesive Polymers in Peroral Peptide Drug Delivery. V. Effect of Poly(acrylates) on the Enzymatic Degradation of Peptide Drugs by Intestinal Brush Border Membrane Vesicles," *International Journal of Pharmaceutics*, 1996, pp. 39-52, vol. 141.

Schilling et al., "Intestinal Mucosal Transport and Metabolism of Insulin," *Department of Industrial and Physical Pharmacy*, Purdue University, W. Lafayette, IN 47907, p. S-157, PDD 7184.

Schipper et al., "Chitosans as Absorption Enhancers of Poorly Absorbable Drugs; 3: Influence of Mucus on Absorption Enhancement," *European Journal of Pharmaceutical Sciences*, 1999, pp. 335-343, vol. 8.

Thanou et al., "Effects of N-Trimethyl Chitosan Chloride, a Novel Absorption Enhancer, on Caco-2 Intestinal Epithelia and the Ciliary Beat Frequency of Chicken Embryo Trachea," *International Journal of Pharmaceutics*, 1999, pp. 73-82, vol. 185.

Tozaki et al., "Use of Protease Inhibitors to Improve Calcitonin Absorption from the Small and Large Intestine in Rats," *J. Pharm. Pharmacol.*, 1998, pp. 913-920, vol. 50.

Uchiyama et al., "Enhanced Permeability of Insulin Across the Rat Intestinal Membrane by Various Absorption Enhancers: Their Intestinal Mucosal Toxicity and Absorption-Enhancing Mechanism of n-Lauryl-$\beta$-D-Maltopyranoside," *J. Pharm. Pharmacol.*, 1999, pp. 1241-1250, vol. 51.

Wade et al., eds., "Polymethacrylates," *Handbook of Pharmaceutical Excipients*, Second Edition, 1994, pp. 362-366, American Pharmaceutical Association, Washington, D.C.

"Aminoalkyl Methacrylate Copolymer E," 1998, pp. 76-77.

* cited by examiner

PHARMACEUTICAL COMPOSITION FOR ORAL USE WITH IMPROVED ABSORPTION

FIELD OF THE INVENTION

The present invention relates to an agent for inhibiting decomposition of a biologically active peptide by a digestive enzyme, which is aminoalkyl methacrylate copolymer E as an effective ingredient. The present invention also relates to an agent for reducing viscosity of the mucous layers distributed over the gastrointestinal mucosa, which is aminoalkyl methacrylate copolymer E as an effective ingredient. The present invention further relates to (1) a method for preventing decomposition of a biologically active peptide by a gastrointestinal enzyme in the gastrointestinal mucosa and/or mucous layers distributed over said mucosa, (2) a method for reducing viscosity of the mucous layers distributed over the gastrointestinal mucosa, (3) a method for reducing viscosity of the mucous layers distributed over the gastrointestinal mucosa and improving permeability of a biologically active peptide in the mucous layers, and (4) a method for improving permeability of a biologically active peptide in the gastrointestinal mucosa, by administering aminoalkyl methacrylate copolymer E. Moreover, the present invention also relates to a pharmaceutical composition for oral use with improved absorption, which comprises a biologically active peptide and aminoalkyl methacrylate copolymer E, and in detail, a pharmaceutical composition for oral use with improved absorption, which comprises a biologically active peptide, aminoalkyl methacrylate copolymer E, and an acidic substance, wherein said three components are brought together and at least said polymer and an acidic substance are uniformly mixed.

BACKGROUND OF THE INVENTION

Drugs that have been orally administered quickly pass through the esophagus to reach the stomach. The stomach lining is made from the three layers of mucosa, tunica muscularis, and tunica serosa. However, in contrast to the small intestine, its effective surface area of absorption is small and therefore, with the exception of some drugs, the stomach lining plays a small role as an absorption site. On the other hand, the human small intestine consists of the duodenum, jejunum, and ileum and is the longest part of the gastrointestinal system and the surface area that is effective in absorption is large. Therefore, it is the site that is suitable for absorption of most drugs. However, epithelial cells, which have a plasma membrane made from a lipid double layer, cover very closely the surface of the gastrointestinal mucosa site and therefore, absorption is greatly restricted in the case of drugs that are very water-soluble and polymer drugs. Moreover, in addition to the gastrointestinal mucosa, the mucous layers that normally cover the gastrointestinal mucosa become a barrier that inhibits gastrointestinal absorption of a biologically active peptide, such as vasopressin and the like. Consequently, drugs that have been orally administered are first absorbed in vivo after passing through the two barriers of the mucous layers that cover the surface of the above-mentioned gastrointestinal mucosa and the mucosa. A biologically active peptide are decomposed by secreted digestive enzymes present in the gastrointestinal mucosa and/or mucous layers and/or mucus distributed over the mucosa before they reach the absorption site and therefore, in addition to the above-mentioned barriers, digestive enzymes form yet another barrier.

Technology with which a biologically active peptide are absorbed from the digestive tract without being decomposed has been an objective for years, but has yet to be established. The following methods are known as technology whereby absorption by oral administration of a biologically active peptide is accelerated:

One of these technologies is the method whereby, for instance, bile acid salts (WO 9606635), which have surfactant activity, amphoteric surfactants such as o-acyl-L-carnitines having acyl groups with 8 to 18 carbons (U.S. Pat. No. 4,537,772), and the like, or anionic surfactants such as sodium lauryl sulfate (SLS), and the like are used, or the method whereby bile acid salts and SLS are concomitantly used (Pharm Res., 7, No. 9, Suppl., S157, 1990). By means of such methods, fluidity of the cell membrane is increased and therefore, absorption of very water-soluble substances is accelerated. However, they are not used for practical purposes because of problems with cytotoxicity (Journal of Controlled Release, 29, 253, 1994).

The method is also given whereby chelation agents such as EDTA (J. Pharm. Pharmacol., 51, No. 11, 1241-50, 1999), EGTA, and the like, or enzyme inhibitors, such as trypsin inhibitors (J. Pharm. Pharmacol., 50, No. 8, 913-20, 1998), and the like, are used. This is a method whereby intercellular space is loosened by withdrawing calcium ions to accelerate membrane permeation by high polymer substances. However, if the concentration is not relatively high, absorption effects are not realized at the biological pH (approximately neutral), and there are also reports of mucous dysfunction by withdrawing calcium ions.

The method is also given whereby insulin is modified by caproic acid (J. Pharm. Sci., 84, No. 6, pp. 682-687, 1995). By means of this method, various a biologically active peptide and higher fatty acids or their esters are modified by synthesis. Therefore, it is a method that is accompanied by a separate complex process of synthesis. Moreover, there is a reduction in peptide activity as a result of modification.

There is also the method whereby polyacrylic acid gel base, such as polycarbophyl, Carbopol, or (meth)acrylic acid-maleic acid copolymer (U.S. Pat. No. 6,004,575), and the like, or polymer substances, such as chitosan, and the like, is used. This method is intended to accelerate absorption of a biologically active peptide by loosening intercellular space. It asserts that polyacrylic acids gel base can inhibit decomposition of a biologically active peptide by a digestive enzyme as a result of forming a chelate with metal ions (Int. J. Pharm., 141, pp. 39-52, 1996). However, this base is very viscous even though the polymer itself is at a relatively low concentration, and therefore, practical application of this base is said to be difficult. Therefore, although the (meth)acrylic acid-maleic acid copolymer in U.S. Pat. No. 6,004,575 is given as one that reduces viscosity of polyacrylic acid gel bases, it appears that because structurally, this polymer has many carboxyl groups, the use of this polymer will lead to an increase in viscosity of the mucous layers distributed over in gastrointestinal mucosa.

It is reported that chitosan accelerates absorption by loosening intercellular space (Int. J. Pharm., 185, 1, pp. 73-82, 1999). However, because chitosan does not have the ability to inhibit enzymes that decompose a biologically active peptide (Int. J. Pharm., 159, pp. 243-253, 1997), or interact with the mucous layers distributed over the gastrointestinal mucosa to reduce substance permeability of the mucous layers (Eur. J. Pharm. Sci., 8, No. 4, 335-43, 1999), it does not appear that sufficient absorption will be obtained even if chitosan is used.

The following methods are further known as technologies whereby aminoalkyl methacrylate copolymer E is used in order to improve absorption by oral administration of drugs:

An invention is described in specific terms in International Publication Pamphlet WO 00/43041A1 relating to a pharmaceutical composition for oral use with improved absorption comprising a drug that is difficult to absorb because it forms a complex with bile acids, which is difficult to absorb, and aminoalkyl methacrylate copolymer E. Moreover, an invention is also disclosed in the same pamphlet relating to a pharmaceutical composition obtained by dissolution or suspension of aminoalkyl methacrylate copolymer E and surfactant in a solvent and spray drying this solution. Nevertheless, there is no disclosure or indication that the aminoalkyl methacrylate copolymer E that is the active ingredient of the present invention has three effects, (1) the ability to inhibit (prevent) decomposition of biologically active peptide by digestive enzymes in the gastrointestinal mucosa and/or mucous layers distributed over this mucosa, (2) the ability to reduce viscosity of the gastrointestinal mucosa and/or mucous layers distributed over this mucosa (the ability to improve permeability of a biologically active peptide in the mucous layers), and (3) the ability to improve permeability of a biologically active peptide in the gastrointestinal mucosa.

An invention relating to a pharmaceutical preparation in powder form for permucosal administration, which comprises polymer drug, aminoalkyl methacrylate copolymer E as cationic polymer, and the like, is disclosed in International Publication Pamphlet WO 00/02574A1. Nevertheless, only a pharmaceutical preparation for pernasal administration is produced in the examples and only the results relating to pernasal mucosa absorption are confirmed, and there is never any disclosure of the effects of aminoalkyl methacrylate copolymer E on absorption of a biologically active peptide by other mucous membranes, particularly absorption of a biologically active peptide when used as a pharmaceutical preparation for oral administration.

On the other hand, aminoalkyl methacrylate copolymer E is a copolymer of methyl methacrylate, butyl methacrylate, and dimethylaminoethyl methacrylate developed by Röhm, and is a polymer substance marketed under the brand name Eudragit™ E100 or Eudragit™ EPO (both by Röhm GmbH). Its average molecular weight is 150,000 (Pharmaceutical Additives Standard, p. 76-77, 1998, Yakuji Nippo Co., Ltd.; Handbook of Pharmaceutical Excipients, Second Edition, p. 362-366, 1994, American Pharmaceutical Association, Washington and the Pharmaceutical Press, London).

Aminoalkyl methacrylate copolymer E is one type of well-known film coating base that is commonly used for masking the bitter taste and color and moisture-proofing, and the like, of caplets and granules, which (1) is quickly dissolved by gastric juices and (2) dissolves in buffers with a pH of 5.0 or lower, but with which the film inflates in buffers with a pH of 5.0 or higher, and the like. Aminoalkyl methacrylate copolymer E has been used in the past for the purpose of masking the bitter taste and color and moisture-proofing drugs, as well as solubilization, and the like, of drugs.

Consequently, there is a need today to present technology with which a biologically active peptide are absorbed without being decomposed in the digestive tract.

DISCLOSURE OF THE INVENTION

Under such technological standards, the present inventors as a result of intense studies for the purpose of developing oral pharmaceutical preparations of biologically active peptides, such as insulin and calcitonin, and the like to discover that in addition to the fact that biologically active peptides are decomposed by enzymes in the digestive tract, permeability of biologically active peptides is reduced (diffusion is reduced) in the mucous layers distributed over the gastrointestinal mucosa. When the present inventors therefore performed studies using Carbopol, which has been known for years as a substance that improves permeability of drugs in the gastrointestinal mucosa, they discovered that Carbopol and components in the mucous layers interact to increase viscosity of the mucous layers. An increase in viscosity of the mucous layers means that the diffusion speed of a biologically active peptide is at the same time reduced and the time until a biologically active peptide pass through the mucous layer to reach the mucosa is prolonged. An increase in viscosity means that the time for which the a biologically active peptide contact decomposing enzymes in the digestive tract is prolonged. Consequently, the inventors believe that an increase in viscosity in the layers of the mucosa reduces permeability of the mucous layers and/or mucosa by a biologically active peptide and therefore, the a biologically active peptide are readily decomposed by digestive enzymes and as a result, there is a reduction in their in vivo adsorption.

With regard to drugs that form a complex that is difficult to absorb with bile acids, the applicant discovered that aminoalkyl methacrylate copolymer E has the ability to inhibit the formation of this complex and/or dissociate this complex and filed a patent application (International Publication Pamphlet WO 00/43041A1). The applicant continued with these studies and discovered that an agent for oral use with improved absorption for increasing drug permeability in the gastrointestinal mucosa and/or mucous layers distributed over the mucosa, which is aminoalkyl methacrylate copolymer E as an effective ingredient, and a pharmaceutical composition comprising aminoalkyl methacrylate copolymer E used in the presence of an acidic substance can improve drug permeability of the gastrointestinal mucosa and/or layers distributed over this mucosa and filed a patent application (PCT/JP01/06135, U.S. Ser. No. 09/907,557 (filed on Jul. 16, 2001)). The inventors of the present invention continued with further studies and newly discovered that aminoalkyl methacrylate copolymer E simultaneously has (1) the ability to inhibit (prevent) decomposition of a biologically active peptide by decomposing enzymes at sites within the lumen over at the gastrointestinal mucosa and/or mucous layers and/or mucus distributed over this mucosa, (2) the ability to reduce viscosity of the gastrointestinal mucosa and/or mucous layers distributed over this mucosa (ability to improve permeability of a biologically active peptide in the mucous layers), and (3) the ability to improve permeability of a biologically active peptide in the gastrointestinal mucosa.

Although the details are still unclear with respect to the cause of said phenomenon, it appears that aminoalkyl methacrylate copolymer E in solution form has the ability to reduce enzyme activity or alter the high-order structure of protein-decomposing enzymes, or protect a biologically active peptide from protein decomposition, by binding with protein-decomposing enzymes to protect [sic] the activity center. Moreover, it appears that said phenomenon is resulted from the fact that aminoalkyl methacrylate copolymer E in solution form reaches the mucous layers and/or mucosa before drug permeation and as a result, interaction between the components of these layers and mucosa and drug is disturbed, or permeability is enhanced as a result of reaction with the components of mucous and a reduction in viscosity and therefore, drug permeability of epithelial cells and/or intercellular space is improved.

The present inventors considered that, as long as aminoalkyl methacrylate copolymer E, which simultaneously possesses the above-mentioned three activities, is used, this was the first time it might be possible to present an oral pharmaceutical preparation of a biologically active peptide that in the past seemed to lose activity in the presence of enzymes in the digestive tract, and they continued with further intense study. As a result, they discovered that when the essential components of aminoalkyl methacrylate copolymer E, biologically active peptide, and acidic substance are brought together and preferably these three components, but at least the aminoalkyl methacrylate copolymer E and acidic substance, are uniformly mixed, these substances can reach the digestive tract lumen or mucous layers and/or mucosa of the digestive tract, and absorption by oral administration of the biologically active peptide is thereby markedly improved. The present invention was completed based on said knowledge.

That is, the present invention presents
1. An agent for inhibiting decomposition of a biologically active peptide, which is aminoalkyl methacrylate copolymer E as an effective ingredient,
2. the agent for inhibiting decomposition according to above-mentioned 1, which is used in the presence of an acidic substance,
3. the agent for inhibiting decomposition according to above-mentioned 1, wherein the digestive enzyme is trypsin or elastase,
4. the agent for inhibiting decomposition according to above-mentioned 1, wherein the amount of aminoalkyl methacrylate copolymer E used is 0.one part by weight or more per one part by weight of a biologically active peptide,
5. the agent for inhibiting decomposition according to above-mentioned 2, wherein the acidic substance is one with which when 1 g of this substance is dissolved in 50 ml of water, pH of this solution is 6 or lower,
6. the agent for inhibiting decomposition according to above-mentioned 2, wherein the amount of the acidic substance added is the amount to neutralize 10% or more of the basic groups of aminoalkyl methacrylate copolymer E,
7. an agent for reducing viscosity of the mucous layers distributed over the gastrointestinal mucosa, which is aminoalkyl methacrylate copolymer E as an effective ingredient,
8. the agent for reducing viscosity according to above-mentioned 7, which is used in the presence of an acidic substance,
9. the agent for reducing viscosity according to above-mentioned 7, wherein the amount of aminoalkyl methacrylate copolymer E used is 0.one part by weight or more per one part by weight of a biologically active peptide,
10. the agent for reducing viscosity according to above-mentioned 8, wherein the acidic substance is one with which when 1 g of this substance is dissolved in 50 ml of water, pH of said solution is 6 or lower,
11. the agent for reducing viscosity according to above-mentioned 8, wherein the amount of the acidic substance added is the amount to neutralize 10% or more of the basic groups of aminoalkyl methacrylate copolymer E,
12. the method for inhibiting decomposition of a biologically active peptide by administering aminoalkyl methacrylate copolymer E to prevent decomposition of a biologically active peptide by a digestive enzyme,
13. the method according to above-mentioned 12, which is used in the presence of an acidic substance,
14. the method according to above-mentioned 12, wherein the digestive enzyme is trypsin or elastase,
15. the method according to above-mentioned 12, wherein the amount of aminoalkyl methacrylate copolymer E is 0.one part by weight or more per one part by weight of a biologically active peptide,
16. the method according to above-mentioned 13, wherein the acidic substance is one with which when 1 g of this substance is dissolved in 50 ml of water, pH of this solution is 6 or lower,
17. the method according to above-mentioned 13, wherein the amount of the acidic substance added is the amount to neutralize 10% or more of the basic groups of aminoalkyl methacrylate copolymer E,
18. a method for reducing viscosity of the gastrointestinal mucosa and/or the mucous layers distributed over said mucosa by administering aminoalkyl methacrylate copolymer E,
19. the method according to above-mentioned 18, which is used in the presence of an acidic substance,
20. a pharmaceutical composition for oral use with improved absorption, which comprises a biologically active peptide and aminoalkyl methacrylate copolymer E,
21. the pharmaceutical composition according to above-mentioned 20, which comprises a biologically active peptide, aminoalkyl methacrylate copolymer E, and an acidic substance, wherein said three components are brought together and at least this polymer and this acidic substance are uniformly mixed,
22. the pharmaceutical composition according to above-mentioned 21, wherein a biologically active peptide, aminoalkyl methacrylate copolymer E, and acidic substance are uniformly mixed,
23. the pharmaceutical composition according to above-mentioned 21 or 22, wherein the amount of aminoalkyl methacrylate copolymer E added is 0.one part by weight or more per one part by weight of a biologically active peptide,
24. the pharmaceutical composition according to above-mentioned 21 or 22, wherein the acidic substance is one with which when 1 g of this substance is dissolved in 50 ml water, pH of this solution is 6 or lower,
25. the pharmaceutical composition according to above-mentioned 21 or 22, wherein the amount of acidic substance added is the amount to neutralize 10% or more of the basic groups of aminoalkyl methacrylate copolymer E,
26. the pharmaceutical composition according to above-mentioned 21 or 22, wherein aminoalkyl methacrylate copolymer E and the acidic substance are granulated,
27. the pharmaceutical composition according to above-mentioned 21 or 22, which is obtained by dissolving and or dissolving aminoalkyl methacrylate copolymer E and an acidic substance in a pharmaceutically acceptable solvent and spray drying this liquid to produce a spray-dried substance, or freeze-drying this liquid to produce a freeze-dried substance after dissolution,
28. the pharmaceutical composition according to above-mentioned 27, wherein aminoalkyl methacrylate copolymer E and the acidic substance are dissolved and/or suspended in a pharmaceutically acceptable solvent,
29. the pharmaceutical composition according to above-mentioned 21 or 22, wherein the form of the pharmaceutical preparation is one or two or more selected from the group consisting of granules, tablets, capsules, and liquid,
30. the pharmaceutical composition according to above-mentioned 21 or 22, wherein the biologically active peptide is one of that is decomposed by a digestive enzyme and/or one of that is difficult to absorb, and
31. the pharmaceutical composition according to above-mentioned 30, wherein the biologically active peptide is calcitonin, insulin, or vasopressin.

The "digestive tract" in the present specification means the small intestine consisting of the duodenum, jejunum, and ileum, the colon consisting of the ascending colon, transverse colon, descending colon, and sigmoid colon, as well as the large intestine consisting of the colon and the rectum.

The "digestive tract lumen" in the present specification means the lumen through which for instance, food and the like pass on the surface of the mucous layers distributed over the surface of the mucosa of the "digestive tract."

(1) The novel uses of the present invention will now be described:

The present invention presents (A-1) inhibition (inhibition [sic]) of decomposition of a biologically active peptide by a digestive enzyme present somewhere in the digestive tract, for instance, the gastrointestinal mucosa and/or mucous layers distributed over said mucosa and/or gastrointestinal lumen that lies over these mucous layers, (A-2) the ability to reduce viscosity of the gastrointestinal mucosa and/or mucous layers distributed over said mucosa, (A-3) improvement of permeability (diffusion) of a biologically active peptide in the mucous layers based on the ability in (A-2), and (A-4) improvement of permeability of a biologically active peptide in the gastrointestinal mucosa, using aminoalkyl methacrylate copolymer E as the active ingredient.

The aminoalkyl methacrylate copolymer E is used alone, or preferably in the presence of an acidic substance. There are no particular restrictions to the amount of said polymer that is used as long as it is the amount that inhibits decomposition of a biologically active peptide, the amount that reduces viscosity of the mucous layers distributed over the gastrointestinal mucosa, or the amount that improves permeability of a biologically active peptide in the gastrointestinal mucosa and/or mucous layers distributed over the mucosa. The amount added (by weight) is usually 10 mg to 3,000 mg, preferably 25 mg to 2,500 mg, further preferably 50 mg to 2,000 mg.

Furthermore, the details of the amount of said polymer that is used and the method by which it is administered will be described in the disclosure of the invention relating to a pharmaceutical composition for oral use with improved absorption.

(2) The invention as it relates to the method of the present invention will now be described below:

Moreover, the present invention presents (B-1) a method of inhibiting (preventing) decomposition of a biologically active peptide by a digestive enzyme present somewhere in the digestive tract, for instance, the gastrointestinal mucosa and/or mucous layers distributed over said mucosa and/or the lumen of the digestive tract that lies over these mucous layers, (B-2) a method for reducing viscosity of the gastrointestinal mucosa and/or mucous layers distributed over said mucosa, (B-3) a method for improving permeability (diffusion) of a biologically active peptide in the mucous layers based on the ability in (B-2), and (B-4) a method for improving permeability of a biologically active peptide in the gastrointestinal mucosa, by administering aminoalkyl methacrylate copolymer E.

Aminoalkyl methacrylate copolymer E is used alone, or preferably in the presence of an acidic substance. There are no particular restrictions to the amount of said polymer that is used as long as it is the amount that inhibits decomposition of a biologically active peptide, the amount that reduces viscosity of the mucous layers distributed over the gastrointestinal mucosa, or the amount that improves permeability of a biologically active peptide in the gastrointestinal mucosa and/or mucous layers distributed over the mucosa. The amount added (by weight) is usually 10 mg to 3,000 mg, preferably 25 mg to 2,500 mg, further preferably 50 mg to 2,000 mg.

Furthermore, details of the amount of said polymer that is used and the method by which it is administered will be described in the disclosure of the invention relating to a pharmaceutical composition for oral use with improved absorption.

The inventors were surprised to find that a pharmaceutical composition based on the above-mentioned invention relating to novel uses of the present invention and invention relating to novel methods is the first pharmaceutical composition to be presented for oral use with improved absorption of a biologically active peptide.

The "brought together" in the present specification means to uniformly mix the aminoalkyl methacrylate copolymer E and acidic substance (preferably further including the biologically active peptide) so that each component is present close together in a solid state or in liquid state within the scope of the purpose of the present invention, that is, such that permeability of the gastrointestinal mucous layers and/or mucosa is improved and absorption by oral administration can thereby be improved. Consequently, the embodiment whereby, for instance, the biologically active peptide is processed to such an extent that the above-mentioned state can be used (for instance, embodiment whereby the biologically active peptide is covered by a water-soluble substance such as saccharide, starch, hydroxypropyl methylcellulose, and the like) in cases where stability of a biologically active peptide is reduced by contact with an acidic substance, and the like, is also within the scope of the invention of the present application.

Figure 1:
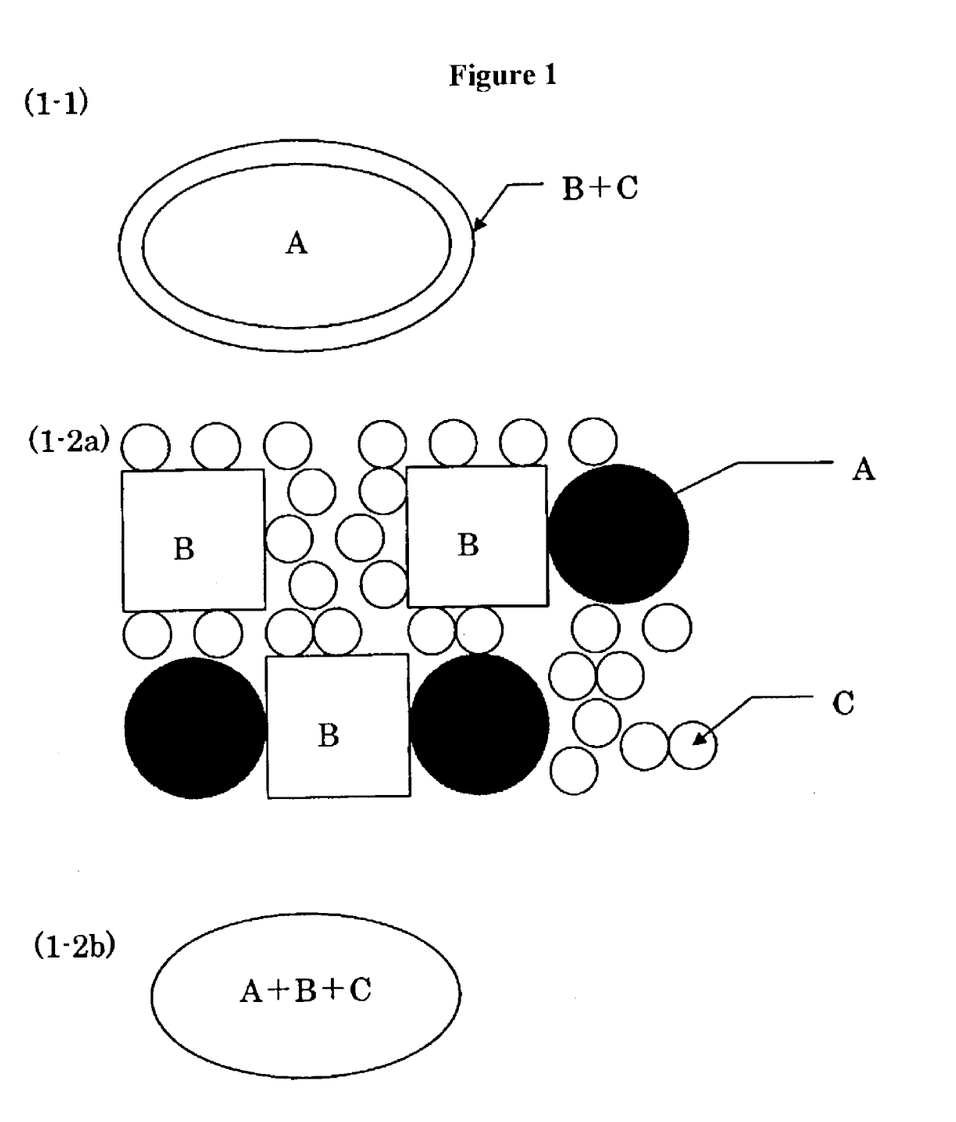

The "uniformly" in the present specification means that as a whole, each component is in a uniform state as shown in FIG. 1(1-2b), even when, for instance, the biologically active peptide, aminoalkyl methacrylate copolymer E, and acidic substance (a biologically active peptide is included as the preferred embodiment) are sporadically present, as shown in FIG. 1(1-2a). On the other hand, the state where each component is maldistributed, as with a three-layered tablets where the biologically active peptide, aminoalkyl methacrylate copolymer E, and acidic substance are each layered, and the like, is not "uniform." Moreover, "uniformly mixed" is the state of being mixed by a method that is well known in the pharmaceutical field. A solid composition produced by physically mixing, spray-drying, freeze-drying, or granulation (wet granulation or dry granulation) of each component, or liquid composition wherein each component has been suspended and/or dissolved in a solvent that is pharmaceutically acceptable, such as water, and the like, are given as examples. FIG. 1 shows some of the embodiments, but the present invention is not limited to the embodiments.

Furthermore, the agent that inhibits decomposition and the agent that reduces viscosity, or the pharmaceutical composition for oral use with improved absorption comprising an agent for inhibiting decomposition or an agent for reducing viscosity, of the present invention can consist of only the above-mentioned aminoalkyl methacrylate copolymer E, or it can be a pharmaceutical preparation form that contains said polymer and a pharmaceutically acceptable carrier.

That is, the agent that inhibits decomposition and the agent that reduces viscosity of the present invention can be made into a conventional pharmaceutical composition by using the above-mentioned polymer as the essential ingredient together with a conventional pharmaceutically acceptable carrier, or the pharmaceutical composition for oral use with improved absorption containing an agent for inhibiting decomposition or an agent for reducing viscosity can be made into a conventional pharmaceutical composition by using a biologically active peptide and aminoalkyl methacrylate copolymer E as the essential ingredients together with a conventional pharmaceutically acceptable carrier. Examples of carriers are fillers, including diluents or stabilizers, such as extenders, binders, disintegrating agents, lubricants, and the like that are normally used in accordance with the form of pharmaceutical preparation that is used, and these are selected and used as needed in accordance with the administration unit form of the pharmaceutical preparation.

A variety of forms can be selected in accordance with the purpose of treatment as the administration unit form of the above-mentioned pharmaceutical preparation, and tablets, pills, powders, liquids, suspensions, emulsions, granules, capsules, injections (liquid or suspension, and the like), and the like are given as typical examples.

(3) The invention as it relates to the pharmaceutical composition for oral use with improved absorption of the present invention will now be described below:

The present invention presents a pharmaceutical composition for oral use with improved absorption comprising a biologically active peptide and aminoalkyl methacrylate copolymer E, preferably a pharmaceutical composition for oral use with improved absorption obtained by uniformly mixing aminoalkyl methacrylate copolymer E and acidic substance, particularly by uniformly mixing acidic substance with this polymer in an amount to neutralize 10% or more of the basic groups of this polymer so that this polymer will be dissolved in sites of the digestive tract that range from being neutral to of weak alkalinity. The pharmaceutical composition for oral use with improved absorption comprising a biologically active peptide and aminoalkyl methacrylate copolymer E (preferably with which an acidic substance has been further uniformly mixed) has the effect of (C-1) making it possible to improve oral absorption of a biologically active peptide that are decomposed in the digestive tract, decomposed by enzymes in the digestive tract, or show reduced permeability in the mucous layers distributed over the gastrointestinal mucosa because this polymer can be dissolved, even in sites of the digestive tract that range from being neutral to of weak alkalinity, (C-2) although a pharmaceutical preparation design that takes into consideration the optical absorption site is necessary because the optimal absorption site varies with the type of biologically active peptide in general, making it possible for the entire digestive tract to serve as the effective site of absorption of a biologically active peptide because aminoalkyl methacrylate copolymer E can be dissolved in of course the small intestine with a large effective absorption surface area, including the duodenum, jejunum, and ileum, of the upper small intestine, as well as the colon of the lower digestive tract (ascending colon, transverse colon, descending colon, and sigmoid colon) with a low water content, and the large intestine, including the rectum and the like, (C-3) making it possible for the aminoalkyl methacrylate copolymer E to inhibit a reduction in permeability of a biologically active peptide in the mucous layers based on interaction between the components of the mucous layers and/or mucosa of the digestive tract and a biologically active peptide, (C-4) making it possible to improve oral absorption of a biologically active peptide as a result of the ability to inhibit and/or the ability to delay decomposition of a biologically active peptide by decomposing enzymes, and the like.

There are no particular restrictions to the biologically active peptide used in the present invention as long as they are peptides, proteins, or their derivatives used for treatment or prevention of disease. Examples of a biologically active peptide are insulin, calcitonin, angiotensin, vasopressin, desmopressin, LH-RH (luteinizing hormone releasing hormone), somatostatin, glucagon, oxytocin, gastrin, cyclosporin, somatomedin, secretin, h-ANP (human atrial natriuretic peptide), ACTH (adrenocorticotropic hormone), MSH (melanocyte stimulating hormone), β-endorphin, muramyl dipeptide, enkephalin, neurotensin, bombesin, VIP (vasoactive intestinal peptide), CCK-8 (cholecystokinin-8), PTH (parathyroid hormone), CGRP (calcitonin gene-related peptide), TRH (thyrotropin releasing hormone), endothelin, hGH (human growth hormone), and cytokines such as interleukin, interferon, colony stimulating factor, tumor necrosis factor, and the like, and their derivatives. These peptides and proteins include natural ones, as well as derivatives that are pharmacologically active and their analogs. For instance, substances that are present in nature, such as salmon calcitonin, human calcitonin, porcine calcitonin, eel calcitonin, and chicken calcitonin, as well as genetic recombination products, and the like, are included among the calcitonin that is the subject of the present invention. Moreover, human insulin, porcine insulin, bovine insulin and their genetic recombination products, and the like, are included among the insulin [that is the subject of the present invention].

There are no particular restrictions to the amount of a biologically active peptide that is added as long as it is the amount that is effective in terms of treatment or prevention of disease.

There are no particular restrictions to the state when aminoalkyl methacrylate copolymer E is mixed in the pharmaceutical composition as long as it is the state where it is brought together with a biologically active peptide and uniformly mixed with the acidic substance as described later. Examples of this state are solids, such as powders, and the like, of this polymer itself, or liquids, such as aqueous solutions wherein said polymer has been suspended and/or dissolved in water, and the like. Conventional methods, for instance, pulverizing, spray-drying, freeze-drying, wet granulation, dry granulation, and the like, can be given as a method for making a powder. It is preferred that the acidic substance described later is added as the auxiliary agent for dissolution of this polymer. Aminoalkyl methacrylate copolymer E can have free amino groups or it can be a soluble salt. In the case of a soluble salt, the preferred state is prepared by spray drying or freeze drying a solution of aminoalkyl methacrylate copolymer E dissolved or dissolved and suspended together with acid. Aminoalkyl methacrylate copolymer E can contain surfactant. There are no particular restrictions to the surfactant that is added as long as it is one that is normally pharmaceutically acceptable and with which water repellency of this polymer is alleviated. Examples of this surfactant are nonionic surfactants (for instance, polyoxyethylene surfactant (for instance, polysorbate 80, polyoxyl stearate 40, lauromacrogol, polyoxyethylene-hydrogenated castor oil (HCO-60), sucrose fatty acid ester, and the like), ionic surfactants (anionic surfactants (for instance, sodium laurylsulfonate and the like), cationic surfactants (for instance, benzalkonium chloride and the like), amphoteric surfactants (lecithin and the like)), and the like. One or two or more of these can be used as needed. There are no particular restrictions to the amount of this surfactant that is added as long as it is the amount that reduces water repellency of this polymer, but it is usually approximately 0.01 to 10 parts by weight, preferably approximately 0.01 to 5 parts by weight, further preferably approximately 0.05 to one part by weight, per one part by weight of this polymer. There are no particular restrictions to the solvent that dissolves or suspends aminoalkyl methacrylate copolymer E (containing surfactant as desired) as long as it is a solvent that is normally pharmaceutically acceptable. Examples are water, organic solvents (for instance, methanol, ethanol, isopropanol, acetone, and the like), mixtures of water and organic solvents, and the like. Extenders, such as lactose, starch, and the like, are given as fillers or additives.

There are no particular restrictions to the amount of aminoalkyl methacrylate copolymer E that is added as long as the correlation with the amount of a biologically active peptide that is added is adjusted as needed, but it is usually at least 0.0one part by weight, preferably 0.1 to 1,000,000 part by weight, more preferably 0.5 to 100,000 part by weight, further more preferably 1 to 100,000 part by weight, per one part by weight of biologically active peptide. The amount added (by weight) is usually 10 mg to 3,000 mg, preferably 25 mg to 2,500 mg, further preferably 50 mg to 2,000 mg. Furthermore, surfactant can also be added to aminoalkyl methacrylate copolymer E for the purpose of accelerating absorption even further. Nonionic surfactants (for instance, polyoxyethylene surfactants (such as polysorbate 80, polyoxyl stearate 40, lauromacrogol, polyoxyethylene-hydrogenated castor oil (HCO-60), sucrose fatty acid ester, and the like), ionic surfactants (anionic surfactants (for instance, sodium laurylsulfonate and the like), cationic surfactants (for instance, benzalkonium chloride and the like), amphoteric surfactant (lecithin and the like)), and the like, are examples of this surfactant. One or two or more of these surfactants can be used as needed.

There are no particular restrictions to the acidic substance that is used in the present invention as long as it is one that is pharmaceutically acceptable and capable of dissolving aminoalkyl methacrylate copolymer E by neutralization of some or all of the basic groups of this polymer in the presence of water. This acidic substance is preferably an inorganic acid and/or organic acid that brings pH of the solution to six or lower when one gram of this substance is dissolved or suspended in 50 ml water. Inorganic acids such as hydrochloric acid, phosphoric acid, potassium dihydrogen phosphate, sodium dihydrogen phosphate, and the like; organic acids such as citric acid, lactic acid, tartaric acid, fumaric acid, phthalic acid, acetic acid, oxalic acid, malonic acid, adipic acid, phytic acid, succinic acid, glutaric acid, maleic acid, malic acid, mandelic acid, ascorbic acid, benzoic acid, methanesulfonic acid, capric acid, caproic acid, caprylic acid, lauric acid, arachidonic acid, erucic acid, linolic acid, linoleic acid, oleic acid, palmitic acid, myristic acid, stearic acid, and the like; aspartic acid, glutamic acid (preferably the L form), cysteine (preferably the L form), arginine hydrochoride, lysine hydrochloride, glutamic acid (preferably the L form) hydrochloride, and the like, are given as examples of the acidic substance used in the present invention. One or a combination of two or more of these can be used.

There are no particular restrictions to the amount of acidic substance added as long as it is the amount that is capable of dissolving aminoalkyl methacrylate copolymer E by neutralization of part or all of the basic groups of this polymer in the presence of water. The amount of this substance that is added is usually the amount to neutralize approximately 10% or more, preferably the amount to neutralize approximately 15% or more, further preferably the amount to neutralize approximately 30% or more, more preferably the amount to neutralize approximately 40% or more, optimally the amount to neutralize 50% or more, of the basic groups of this polymer. It is ideal if at least 50% acidic substance is also present because the spray-dried product will be easy to handle during production with there being no aggregation, even with long term storage. The amount of this acidic substance is adjusted as needed taking into consideration solubility and acidity of this substance, but is usually 0.005 to 50 parts by weight, preferably 0.01 to 30 parts by weight, further preferably 0.03 to 10 parts by weight, per one part by weight of aminoalkyl methacrylate copolymer E. Furthermore, when 312.5 g of 1 mole/liter hydrochloric acid are added to 500 g Eudragit E and spray dried as an example of the acidic substance used in the present invention, the amount of acidic substance can be calculated by the following formula (I):

$$\frac{1 \times 312.5}{1000}\text{(Number of moles hydrochloric acid)} = \frac{X}{\text{KOH(56)}}\text{(Number of moles KOH)} \quad \text{Formula (I)}$$

X=17.49 g. However, this is the amount in 500 g and therefore, it is divided by 500 to obtain X/1 g Eudragit E=35 mg KOH.

The alkali value in 1 g Eudragit E is actually 163 to 198 mg KOH and therefore, the amount of acid added at this time is 15 to 20% of the amount to neutralize all of the alkali.

There are no particular restrictions to the uniform mixing of aminoalkyl methacrylate copolymer E and an acidic substance used in the present invention as long as it is the state where they are brought together with a biologically active peptide and uniformly mixed and it is possible to realize the embodiment wherein aminoalkyl methacrylate copolymer can be dissolved by the acidic substance in the presence of water. The state wherein biologically active peptide, this polymer, and this acidic substance are uniformly mixed is preferred as this state. The embodiment whereby mixing is performed by a conventional method is given as this state. For instance, the embodiment wherein a powder is produced by a conventional method, such as spray drying, and the like, using aminoalkyl methacrylate copolymer E prepared by the method of mixing the above-mentioned aminoalkyl methacrylate copolymer E that has already been described, or a liquid of aminoalkyl methacrylate copolymer E and an acidic substance, or aminoalkyl methacrylate copolymer E and an acidic substance together with biologically active peptide, dissolved and/or suspended in a solvent that is pharmaceutically acceptable (for instance, water, alcohol (methyl, ethyl, propyl, butyl, and the like) or their mixtures, and the like), the embodiment whereby aminoalkyl methacrylate copolymer E and an acidic substance are mixed or granulated by conventional methods to make a mixture, or the embodiment of a liquid of aminoalkyl methacrylate copolymer E and an acidic substance dissolved and/or suspended in a solvent that is pharmaceutically acceptable, and the like, and in addition to the above-mentioned embodiments, embodiments wherein biologically active peptide is mixed, and the like are given. There are no special restrictions to the pharmaceutical composition with which these embodiments can be specifically realized as long as it is a form of pharmaceutical preparation that can be orally administered. Examples of the pharmaceutical preparation are powders, tablets, capsules, liquids, suspensions, emulsions, capsules filled with liquids, suspensions, emulsions, and so forth, and the like. The method of producing this pharmaceutical preparation can be a conventional method. Specifically, a pharmaceutical preparation that is made such that aminoalkyl methacrylate copolymer E and an acidic substance are present in close proximity to the biologically active peptide is given as a preferred example. Solutions/suspensions in which aminoalkyl methacrylate copolymer E and an acidic substance are dissolved and/or suspended in a pharmaceutically acceptable solvent, capsules obtained by filling the above-mentioned solution/suspension in capsules, such as gelatin capsules, and the like are examples. Mixtures obtained by mixing aminoalkyl methacrylate copolymer E and an acidic substance by a conventional method and then mixing this mixture with a biologically active peptide are examples of mixtures. Granulation product obtained by mixing aminoalkyl methacrylate copolymer E and an acidic substance, adding pharmaceutically acceptable solvent, such as water and the like, or adding, for instance, hydroxypropylmethyl cellulose and the like as binder as needed and granulating [this mixture] are given as a granulation product. Tablets obtained by mixing pharmaceutical fillers with the above-mentioned mixture or granulation product and tableting, capsules wherein the above-mentioned granulation product is filled in, for instance, gelatin capsules, are examples of tablets or capsules. Enteric-coated pharmaceutical preparations obtained by coating the above-mentioned granulation product with an enterosoluble substance (for instance, a 1:1 copolymer of methyl methacrylate and methacrylic acid (brand name: Eudragit™ L, Röhm GmbH), a 2:1 copolymer of methyl methacrylate and methacrylic acid (brand name: Eudragit™ S, Röhm GmbH), a 1:1 copolymer of ethyl acrylate and methacrylic acid (brand name: Eudragit™ LD-55, Röhm GmbH), hydroxypropylmethyl cellulose phthalate, hydroxypropylmethyl cellulose acetate succinate, carboxymethylethyl cellulose, cellulose acetophthalate, shellac, zein, and the like), or enteric-coated pharmaceutical preparations obtained by coating tablets obtained by tableting the above-mentioned granulation product with an enterosoluble substance (same as previously mentioned) are examples of enteric-coated pharmaceutical preparations. In this case, pharmaceutical additives, such as filler, disintegrating agent, binder, lubricant, fluidizer, dispersant, suspending agent, emulsifier, preservative, stabilizer, and the like, can be added as needed.

The ratio at which the biologically active peptide, aminoalkyl methacrylate copolymer E, and an acidic substance are mixed in the pharmaceutical composition is 0.1 to 1,000,000 parts by weight (preferably 0.5 to 100,000 parts by weight, further preferably 1 to 100,000 parts by weight) per one part by weight the amount of a biologically active peptide that is effective in terms of treatment or prevention of disease, and the amount of acidic substance to neutralize 10% or more (preferably 15% or more, further preferably 30% or more, more preferably 40% or more, ideally 50% or more) of the basic groups of the above-mentioned polymer. It is also possible to use a mixture of the above-mentioned three components wherein there is 0.1 to 1,000,000 parts by weight (preferably 0.5 to 100,000 parts by weight, further preferably 1 to 100,000 parts by weight) aminoalkyl methacrylate copolymer E per one part by weight the amount of biologically active peptide that is effective in terms of treatment or prevention of disease, and 0.005 to 50 parts by weight (preferably 0.01 to 30 parts by weight, further preferably 0.03 to 10 parts by weight) acidic substance in the pharmaceutical composition.

The pharmaceutical composition for oral use with improved absorption of the present invention can be used with a variety of conventional pharmaceutical preparations. Specific pharmaceutical preparations are, for instance, the usual pharmaceutical preparations (tablets, capsules, liquid, powders, granules, and the like), sustained-release pharmaceutical preparations (for instance, refer to International Publication Pamphlet No. WO 94/06414), colon-released pharmaceutical preparations (for instance, refer to International Publication Pamphlet WO 95/28963), timed-release or pulse-released pharmaceutical preparations (for instance, refer to WO 01/78686A1: PCT/JP01/03229 (filed on Apr. 16, 2001), U.S. Ser. No. 09/834,410 (filed on Apr. 12, 2001), International Publication Pamphlet WO 93/05771), micro-particle pharmaceutical preparations (for instance, refer to National Publication No. Hei 10-511957), mucosa-adhering pharmaceutical preparations (for instance, refer to Japanese Kokai Patent No. Hei 5-132416), and the like. The hydrogel-forming sustained-release pharmaceutical preparation in International Publication WO 94/06414, colon-released pharmaceutical preparation in International Publication WO 95/28963 (for instance, a pharmaceutical preparation wherein a mixture of a granulation product obtained by granulation of the pharmaceutical composition for oral use with improved absorption of the present invention and saccharide that is decomposed by enterobacilli to generate an organic acid (for instance, lactulose and the like) is coated with a polymer substance that is dissolved by organic acids and then coated with a nonionic substance, such as hydroxypropyl methyl cellulose and the like, as needed, and further coated with enterosoluble substance, or a pharmaceutical preparation obtained by coating tablets that have been obtained by tableting the above-mentioned mixture with a polymer substance that is dissolved by organic acids, coating with a nonionic substance such as hydroxypropyl methyl cellulose, and the like, as needed, and further coating with an enterosoluble substance), and the timed-release pharmaceutical preparation in above-mentioned WO 01/78686A1 are preferred. Moreover, when polyethylene oxide is used as the sustained-releasable base, inventions relating to stable oral pharmaceutical compositions obtained by adding yellow ferric oxide and/or red ferric oxide as stabilizer (International Publication Pamphlet WO 01/10466A1, U.S. Ser. No. 09/629,405) can be used in combination with one another. Furthermore, the components and amounts of components added, and the like, related to each invention can be based on the inventions in the respective gazette or pamphlet.

The dose of the agent that inhibits decomposition, the agent that reduces viscosity, or pharmaceutical composition for oral use with improved absorption of the present invention is selected and determined as needed in accordance with the dose of concomitant biologically active peptide, and the like. The daily adult dose should usually be approximately 0.001 to 100 mg per 1 kg body weight, and this dose can be administered once or divided into several times, for instance, 2 to 4 times, per day in accordance with the biologically active peptide that is used and the like.

Moreover, the dose of the agent that inhibits decomposition, the agent that reduces decomposition or a pharmaceutical composition for oral use with improved absorption of the present invention is selected as needed based on the method of its use, patient age, sex and other conditions, extent of disease, and the like, but it normally should be the effective amount with which the natural ability of the biologically active peptide contained in the active ingredients can be realized. This amount is selected as needed in accordance with the type of biologically active peptide that is used and there are no special restrictions. However, the daily adult dose should usually be approximately 0.001 to 100 mg per 1 kg body weight, and this pharmaceutical preparation can be administered once or divided into several times, for instance, 2 to 4 times, per day.

The above-mentioned pharmaceutical preparation can be obtained by, for instance, making a biologically active peptide into a pharmaceutical preparation by conventional methods. This can be a coated tablet form coated by conventional methods or a solid dispersion form that has been obtained using the above-mentioned biologically active peptide. Preparation of this solid dispersion form can be accomplished in accordance with conventional methods by, for instance, dissolving or suspending a biologically active peptide and aminoalkyl methacrylate copolymer E in an appropriate solvent and then removing the solvent.

Furthermore, when an agent that inhibits decomposition, an agent that reduces viscosity, or a pharmaceutical composition for oral administration with improved absorption of the present invention is prepared as a pharmaceutical preparation separate from the biologically active peptide, it should be administered simultaneously with the biologically active peptide.

BRIEF DESCRIPTION OF THE DRAWINGS

FIG. 1 is a schematic representation showing on embodiment of the pharmaceutical composition of the present invention. FIG. (1-1) is a schematic representation showing a preparation form (for instance, granules, powder, capsule filled with these, liquid, suspension, emulsion, capsule filled with liquid, suspension, emulsion, and so forth, and the like can be given) wherein a core comprising drug (A in the figure) is coated by a layer in which aminoalkyl methacrylate copolymer E (B in the figure) and an acidic substance (C in the figure) have been uniformly mixed. FIGS. (1-2a) and (1-2b) are schematic representations showing the same composition of one embodiment of the present invention. By means of this embodiment of the present invention, even a composition where microscopically, each component of drug (A in the figure), aminoalkyl methacrylate copolymer E (B in the figure) and an acidic substance (C in the figure) is not seen to exist uniformly dispersed with the other components, as shown in FIG. (1-2a), is a composition wherein macroscopically, each component exists uniformly mixed with the other components as a whole. The preparation form of this state can be, for instance, powder, granules, capsules filled with these or granulation product or mixture, as well as tablets that have been obtained by their compression molding, capsules filled with liquid, suspension, emulsion, and so forth, and the like.

PREFERRED EMBODIMENTS OF THE INVENTION

Studies, experiments and examples will now be used to describe the invention, but the present invention is not limited to these examples.

Furthermore, aminoalkyl methacrylate copolymer E of the present invention that was used was prepared as described below, but aminoalkyl methacrylate copolymer E of the present invention is not limited to these references.

[Reference 1] First, 1,650 g Eudragit™ E100 (Röhm GmBH) and Tween 80 at a ratio of 10:1 were dissolved in 12,000 g 1 mole/liter aqueous hydrochloric acid•ethanol mixture (5:12) to make the spraying liquid. The spraying liquid was spray dried under conditions of a spraying speed of 30 g/minute, inlet temperature of 85° C., and outlet temperature of 62 to 66° C. using an L-8 spray drying device (Ohkawara Kakohki Co., Ltd.). A white powder was obtained after drying for 24 hours at 40° C. (E-SD hereafter; used in the examples, studies, comparative examples, and the like, below unless otherwise noted).

[Reference 2] 1,500 g Eudragit™ E100 and 150 g Tween 80 were dissolved in a mixture of 9,000 g ethanol and 3,000 g 1 mole/liter hydrochloric acid to make the spraying liquid. The spraying liquid was spray dried under conditions of a spraying speed of 30 g/minute, inlet temperature of 85° C., and outlet temperature of 62 to 66° C. using an L-8 spray drying device (Ohkawara Kakohki Co., Ltd.). A white powder was obtained after drying for 24 hours at 40° C. When 1 g of this product was added to 15 ml purified water, it completely dissolved. Moreover, this product was stable with no aggregation seen during storage.

[Reference 3] First, 2.9 g Eudragit™ EPO, which is a fine powder of Eudragit™ E, were added to 50 g purified water to obtain the sample liquid. When 650 mg citric acid were added to this sample liquid, the Eudragit™ E in the sample liquid completely dissolved. A solution of 0.25 g Tween 80 dissolved in this liquid was freeze-dried using an FD-81 freeze-drying device (Tokyo Rika-Kikai Co., Ltd.) to obtain a white freeze-dried product. When 1 g of this product was added to 15 g purified water, it completely dissolved.

[Reference 4] First, 2.9 g Eudragit™ EPO were dissolved in 50 g purified water to obtain the sample liquid. When 650 mg tartaric acid were added to this sample liquid, the Eudragit™ E in the sample liquid completely dissolved. A solution of 0.29 g Tween 80 dissolved in this liquid was freeze-dried as in Reference 3 to obtain a white freeze-dried product. When 1 g of this product was added to 15 g purified water, it completely dissolved.

[Reference 5] First, 3.3 g Eudragit™ EPO were dissolved in 50 g purified water to obtain the sample liquid. When 650 mg D,L-malic acid were added to this sample liquid, the Eudragit™ E in the sample liquid completely dissolved. A solution of 0.33 g Tween 80 dissolved in this liquid was freeze-dried as in Reference 3 to obtain a white freeze-dried product. When 1 g of this product was added to 15 g purified water, it completely dissolved.

[Study 1] <Improving Effect on Diffusion/Permeation in the Gastrointestinal Mucous Layers>

A 10% mucin solution was made by dissolving 500 mg porcine stomach-derived mucin powder in 5 ml phosphate buffer (liquid A). Then 400 mg E-SD were dissolved in 5 ml phosphate buffer to make an 8% E-SD solution (liquid B). Moreover, 25 mg Carbopol (Acros Co., Ltd.) were dissolved in 5 ml phosphate buffer to make a 0.5% Carbopol solution (liquid C). Liquid A, and liquid B or liquid C were mixed and quickly shook. Viscosity of the solution 0 hours and 3 hours after mixing was determined by a viscometer.

(Results and Discussion)

The results that were obtained are shown in Table 1.

TABLE 1

| | 0 h (% of initial) | 3 h (% of initial) |
|---|---|---|
| E-SD (Liquid B) | 100 | 79.3 |
| Carbopol (Liquid C) | 100 | 138.9 |

It became clear that there is a reduction in mucin-derived viscosity when the E-SD solution and mucin solution were mixed. On the other hand, a reduction in mucin-derived viscosity was not observed and instead a tendency toward an increase was seen with the Carbopol, which has thus far been reported to have absorption-accelerating activity. Consequently, it was indicated that diffusion of a biologically active peptide to the mucous layers is increased due to a reduction in viscosity of the gastrointestinal mucous layers when aminoalkyl methacrylate copolymer E acts on gastrointestinal mucin layers.

<Experiment 1: Experiment Relating to Gastrointestinal Absorption of Insulin>

Laparotomy under pentobarbital (brand name Somnopentyl, Schering-Plough Corporation) was performed on Wistar male rats (10 weeks old) and a large intestine loop was made by binding the colon portion and the anal portion with thread.

Example 1

First, 6 mg bovine insulin and 400 mg E-SD were dissolved (2% E-SD solution) in 16 ml normal saline to prepare the solution of the present invention. This solution was administered to the large intestine and small intestine loop in an amount corresponding to 100 µg/kg insulin. Then 0.25 ml blood was collected from the jugular vein 0, 0.5, 1, 1.5, 2 and 3 hours after administration and the plasma glucose concentration was determined. The reduction in the plasma glucose concentration (D, % of initial*h) up to three hours after administration was calculated with the plasma glucose concentration before administration being 100. D was calculated by subtracting the plasma glucose area under concentration (% of initial*h) up to 3 hours after administration from the AUC with administration of normal saline only.

On the other hand, by way of comparison, a liquid of 6 mg bovine insulin dissolved in 20 ml normal saline liquid was administered to a large intestine loop in an amount corresponding to 600 µg/kg insulin, or as the control, 2 ml normal saline were administered to a large intestine loop and the plasma glucose concentration was determined as described above (Glucose CII Test Wako, Wako Pure Chemical Industries, Ltd.).

(Results and Discussion)

The results that were obtained are shown in Table 2.

TABLE 2

|  | AUC (% of initial*h) | D (% of initial*h) |
|---|---|---|
| Control (normal saline) | 381.84 ± 56.13 |  |
| Comparison (E-SD not administered) | 368.84 ± 63.19 | 13.00 |
| Example 1 | 301.82 ± 47.81 | 80.02 |

Although there was not an obvious reduction in the glucose level when only insulin was administered, a reduction in the glucose level was confirmed when both insulin and E-SD were administered. Consequently, this indicates that absorption of insulin by oral administration is improved when aminoalkyl methacrylate copolymer E and insulin are administered together.

<Experiment 2: Experiment Relating to Gastrointestinal Absorption of Vasopressin>

Laparotomy under pentobarbital (brand name Somnopentyl, Schering-Plough Corporation) was performed on Wistar male rats (10 weeks old) and a small intestine loop was made by binding the Treitz's ligament section and ileocecal junction with thread. Moreover, a large intestine loop was made by binding the colon part and the anal part with thread.

Example 2

First, 0.2 mg Arg$^8$-vasopressin and 400 mg E-SD were dissolved in 20 ml normal saline to prepare the solution of the present invention. This solution was administered to the large intestine and small intestine loops in an amount corresponding to 100 µg/kg Arg$^8$-vasopressin. Then 0.4 ml blood was collected from the jugular vein 0.5, 1, 1.5 and 2 hours after administration and the plasma Arg$^8$-vasopressin concentration was determined.

On the other hand, by way of comparison, a solution of 0.2 mg Arg$^8$-vasopressin dissolved in 20 ml normal saline was administered to the large intestine and small intestine loops in an amount corresponding to 100 µg/kg in terms of Arg$^8$-vasopressin and the plasma Arg$^8$-vasopressin concentration was determined as described above.

(Results and Discussion)

The results that were obtained are shown in Table 3.

TABLE 3

|  |  | AUC (% of initial*h) |
|---|---|---|
| Comparison | Small intestine administration | 1.949 ± 0.76 |
|  | Large intestine administration | 1.563 ± 0.71 |
| Example 2 | Small intestine administration | 3.325 ± 0.83 |
|  | Large intestine administration | 7.652 ± 4.53 |

When compared to the case in which vasopressin only was administered, there was a significant increase in the AUC when vasopressin and E-SD were both administered, and the increase in the AUC was marked with large intestine administration. Consequently, this indicates that E-SD improves absorption by oral administration of vasopressin.

<Experiment 3: Experiment Relating to Improvement of Gastrointestinal Absorption of Calcitonin>

Laparotomy under pentobarbital (brand name Somnopentyl, Schering-Plough Corporation) was performed on SD male rats (5 weeks old) and a small intestine loop was made by binding the Treitz's ligament section and ileocecal junction with thread. Moreover, a large intestine loop was made by binding the colon part and the anal part with thread.

Example 3

First, 1.5 µg salmon calcitonin (sCT) and 400 mg or 200 mg E-SD were dissolved in 20 ml aqueous 1% gelatin solution to prepare the solution of the present invention. This solution was administered to the large intestine and small intestine loops in an amount corresponding to 0.6 µg/kg sCT. Then 0.4 ml blood was collected from the jugular vein 0 1, 2, 3 and 4 hours after administration and the plasma calcium concentration was determined.

On the other hand, by way of comparison, a solution of 1.5 µg sCT dissolved in 20 ml aqueous 1% gelatin solution was administered to the large intestine and small intestine loops in an amount corresponding to 0.6 µg/kg in terms of sCT, or only aqueous 1% gelatin solution was administered, and the plasma calcium concentration was determined as described above. Moreover, the same study as described above was conducted using 100 mg Carbopol sodium salt in place of E-SD.

(Results and Discussion)

The results that were obtained are shown in Table 4.

TABLE 4

|  |  | AUC (% of initial*h) | D (% of initial*h) |
|---|---|---|---|
| 1% gelatin |  | 404.52 ± 7.91 |  |
| Control | Small intestine administration | 421.43 ± 13.54 | −16.91 |
|  | Large intestine administration | 416.17 ± 3.20 | −11.65 |

TABLE 4-continued

|  |  | AUC (% of initial*h) | D (% of initial*h) |
|---|---|---|---|
| Example 3 | Small intestine administration | 363.44 ± 19.42 | 41.08 |
|  | Large intestine administration | 362.63 ± 29.73 | 41.89 |
| Carbopol |  | 393.41 ± 13.36 | 11.11 |

Although an obvious reduction in the plasma calcium concentration with administration of sCT only was not seen, when sCT and E-SD were both administered, a reduction in the plasma calcium concentration by a concentration of 1% or more was seen in the large intestine and a reduction in the plasma calcium concentration by a concentration of 2% or more was seen in the small intestine. Nevertheless, the result was small with the Carbopol that was administered by way of comparison.

<Experiment 4: Inhibiting effect on Decomposition by Digestive Enzymes>

[Control]

First, 0.3 ml phosphate buffer (PBS) solution (1 mg/ml) of N-α-benzoylarginine ethyl ester, which is a specific substrate of trypsin, was added to a mixture of 0.3 ml of a PBS solution of trypsin (0.048 mg/ml) and 1.5 ml PBS, and the amount of substrate in the sample liquid up to 20 minutes after addition was quantitatively determined by UV determination (256 nm). Assuming that the enzyme decomposition reaction is by a linear expression, the substrate decomposition speed constant K (%/min) was calculated by calculating the slope of the time-residual substrate curve.

Example 4

First, 0.3 ml PBS solution (1 mg/ml) of N-α-benzoylarginine ethyl ester was added to a mixture of 0.3 ml of a PBS solution of trypsin (0.048 mg/ml) and 1.5 ml aqueous E-SD solution, and the amount of substrate in the sample liquid after addition was determined, and the K value was calculated as described above. Furthermore, three types of aqueous E-SD solution were prepared so that the E-SD concentration in the sample liquid would be 5, 10 and 20 mg/ml, respectively.

(Results and Discussion)

The results that were obtained are shown in Table 5.

TABLE 5

|  | E-SD (mg/ml) | K (%/min) |
|---|---|---|
| Control | 0 | 15.32 |
| Example 4 | 5 | 12.54 |
|  | 10 | 10.41 |
|  | 20 | 7.92 |

The K value decreased dependent on the amount of E-SD added, and when 20 mg/ml E-SD were added, the K value dropped to approximately half what it was when none was added. These results indicate that there is a reduction in enzyme activity of trypsin with the addition of E-SD. Consequently, this shows that aminoalkyl methacrylate copolymer E to which acid has been added is useful as an inhibitor of decomposition of a biologically active peptide and proteins by digestive enzymes.

[Study 2] <Confirmation of Changes in the High-Order Structure of a Gastrointestinal Enzyme>

The status of the secondary structure of a phosphate buffer solution (0.6 mg/mL) of trypsin was studied by determining the CD spectrum within a wavelength region of 190 to 250 nm using a circular dichroism dispersion meter (JASCO). Furthermore, after mixing the equivalent amount of phosphate buffer solution (0.6 mg/mL) of trypsin and phosphate buffer solution (10 mg/mL) E-SD and setting the mixture aside for 30 minutes, the CD spectrum was similarly determined using the circular dichroism dispersion meter in order to study structural changes of the trypsin.

(Results and Discussion)

Figure 2:
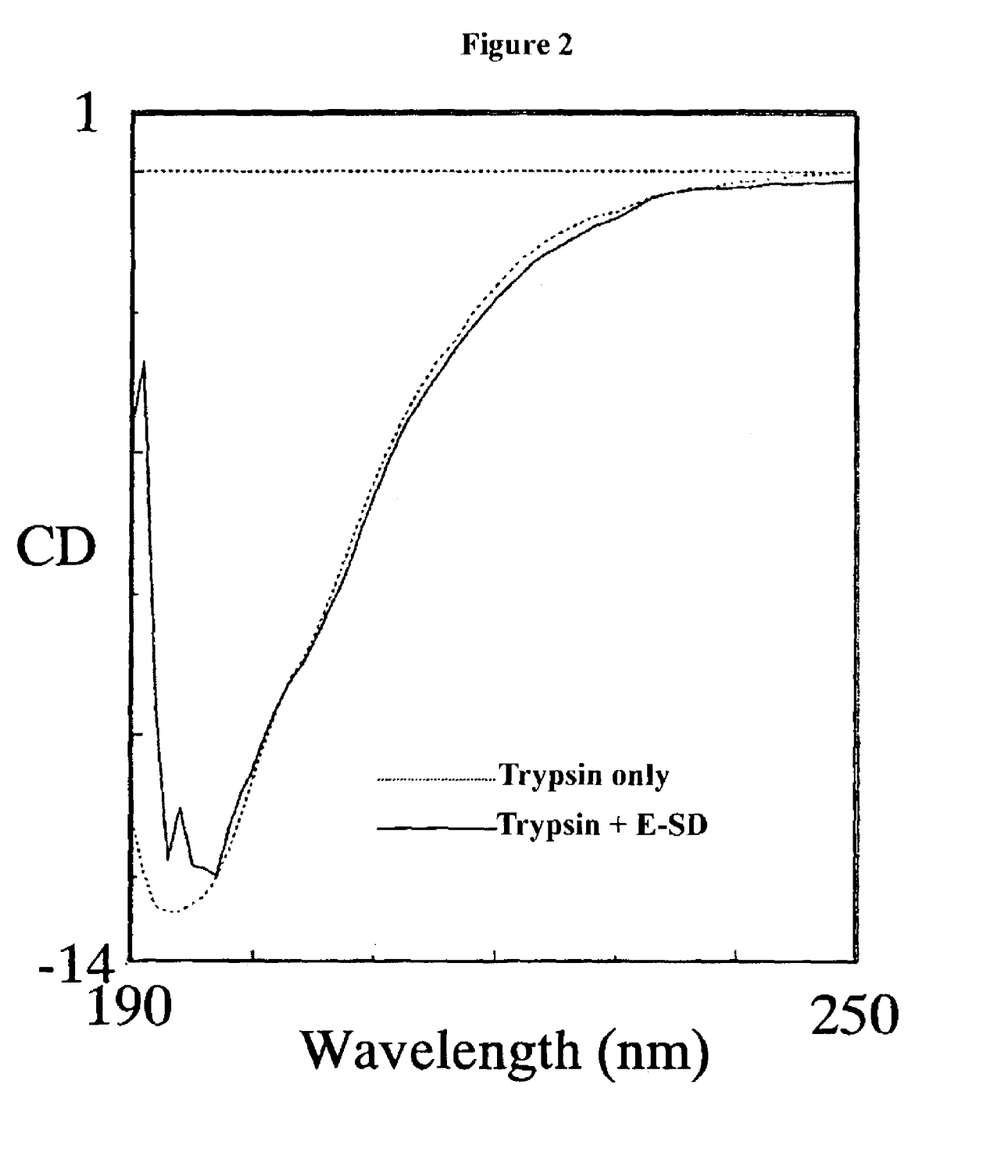
FIG. 2 is a chart showing the secondary structural spectrum of trypsin that was determined using a circular dichroism in order to chart changes in structure of trypsin before and after mixing when 1,650 g Eudragit E100 (brand name, Röhm GmbH) and Tween 80 at a ratio of 10:1 were dissolved in 12,000 g aqueous 1 mole/liter hydrochloric acid solution•ethanol mixture (5:12) and the spray-dried white powder (refer to Reference 1 "E-SD") was mixed with trypsin.

The results that were obtained are shown in FIG. 2.

Obvious changes in the spectrum of the secondary structure of trypsin from a circular dichroism dispersion meter before and after mixing with E-SD could not be confirmed. This therefore indicates that it is possible that the ability of E-SD to inhibit trypsin enzyme activity is not the result of alteration of the structure of the enzyme itself.

[Study 3] <Confirmation of Interaction Between Digestive Enzymes and E-SD>

Changes over time in distribution of absorbance at 280 nm of a phosphate buffer solution (1 mg/mL) and a 1:1 mixture of or trypsin solution (0.095 mg/mL) and E-SD solution (2.5 mg/mL) were determined every 15 minutes using a molecular interaction analysis system based on ultracentrifugation (XL-A, Beckman Coulter, Inc.). The number of rounds was 45,000 rpm. The results were analyzed by the time-derivative method and the apparent sedimentation coefficient s and its distribution g (s) were calculated.

(Results and Discussion)

Figure 3:
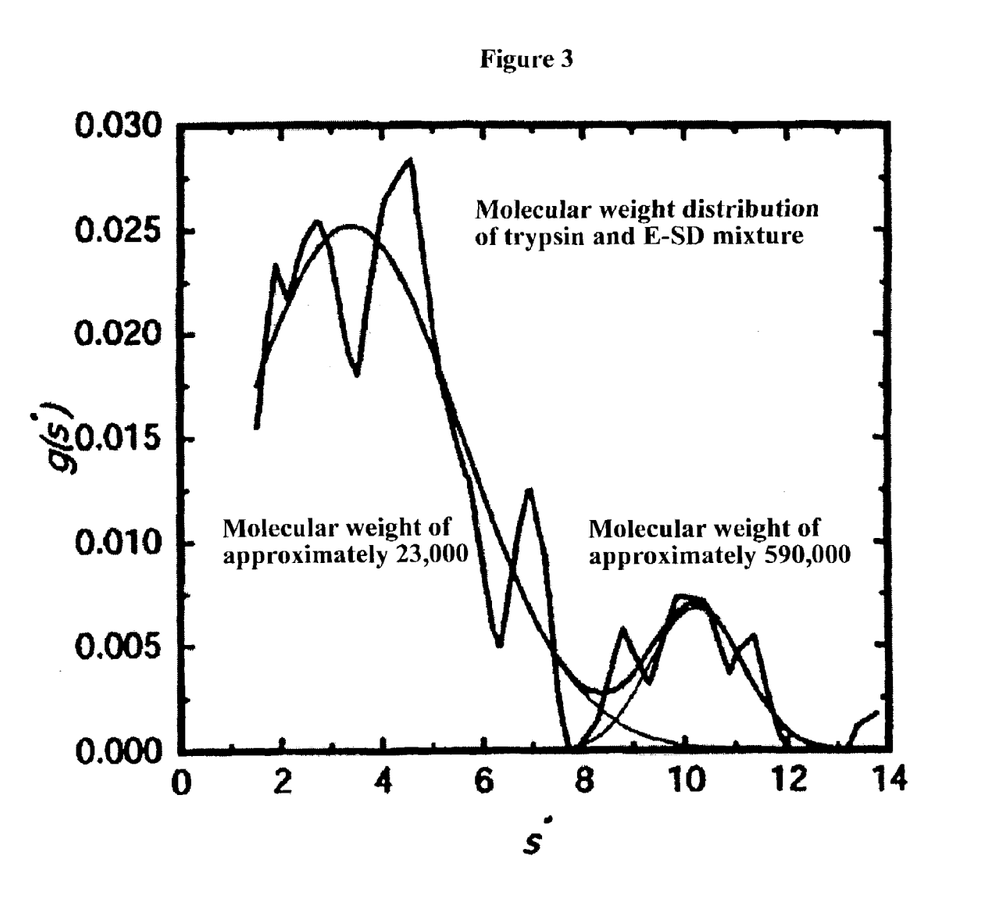
FIG. 3 is a drawing showing changes in molecular weight distribution of trypsin as determined using a molecular interaction analysis system based on ultracentrifugation in order to chart changes in trypsin structure before and after mixing when trypsin and E-SD were mixed. S' is the sedimentation coefficient, and molecular weight is calculated based on the peak value.

The results that were obtained are shown in FIG. 3.

It was clear from the determination results that a compound with a molecular weight of approximately 590,000, not trypsin only (molecular weight of approximately 23,000) is present in the mixture. It was also clear from the size of this molecular weight that the trypsin and E-SD are present in some form of association. The results in Studies 2 and 3 indicated that there is a possibility that interaction between E-SD and trypsin is not accompanied by structural changes in the trypsin and this interaction inhibits the ability of trypsin to decompose proteins.

<Experiment 5: Inhibiting Effect on Decomposition by Digestive Enzymes 2>

[Control]

First, 0.6 ml phosphate buffer (PBS) solution (0.2 mg/ml) of succinyl-(L-alanyl)$_3$-4-nitroanilide, which is a specific substrate of elastase, was added to a mixture of 0.1 ml of a PBS solution of elastase (0.021 mg/ml) and 1.4 ml PBS, and the amount of substrate in the sample liquid up to 20 minutes after addition was quantitatively determined by UV determination (405 nm). Assuming that the enzyme decomposition reaction is by a linear expression, the substrate decomposition speed constant K (%/min) was calculated by calculating the slope of the time-residual substrate curve.

Example 5

First, 0.6 PBS solution (0.2 mg/ml) of succinyl-(L-alanyl)$_3$-4-nitroanilide was added to a mixture of 0.1 ml of a PBS solution of elastase (0.021 mg/ml) and 1.4 ml aqueous E-SD solution, the amount of substrate in the sample liquid after addition was determined, and the K value was calculated as described above. Furthermore, three types of aqueous E-SD solution were prepared so that the E-SD concentration in the sample liquid would be 5, 10 and 20 mg/ml, respectively.

(Results and Discussion)
The results that were obtained are shown in Table 6.

TABLE 6

|  | E-SD (mg/ml) | K (%/min) |
|---|---|---|
| Control | 0 | 20.68 |
| Example 5 | 5 | 16.50 |
|  | 10 | 12.40 |
|  | 20 | 9.28 |

The K value decreased dependent on the amount of E-SD added, and when 20 mg/ml E-SD were added, the K value dropped to approximately half what it was when none was added. These results indicate that there is a reduction in enzyme activity of elastase with the addition of E-SD. Consequently, this shows that aminoalkyl methacrylate copolymer E to which acid has been added is useful as an inhibitor of decomposition of a biologically active peptide and proteins by digestive enzymes.

<Experiment 6: Improvement of Absorption of Insulin by Oral Administration>

[Control]

First, 500 U insulin (17.8 mg) were sealed in hard gelatin capsules (#0, CAPSUGEL). This capsule was orally administered together with 30 ml water to beagles (15 to 24 months old) under fasting conditions. Approximately 2 ml blood were collected from the veins of the front limbs before administration and over time up to 8 hours after administration and the plasma glucose concentration (mg/dl) was determined by a glucose determination kit (Glucose CII Test Wako, Wako Pure Chemical Industries, Ltd.). The plasma glucose reduction (D, % of initial*h) up to 8 hours after administration and the minimum glucose concentration (Cmin, % of initial) were calculated with the plasma glucose concentration before administration being 100. D was calculated by subtracting the plasma glucose area under concentration AUC (% of initial*h) up to 8 hours after administration from the AUC when insulin was not administered=100 (% of initial)*8 (h)=800 (% of initial*h).

Example 6

First, 500 U (17.8 mg) insulin, 125 mg F-SD, 50 mg DL-malic acid, and 207.2 mg polyethylene glycol 6000 (PEG6000 hereafter) were mixed and molded under a tableting pressure of 40 kg/cm$^2$ using an oil press to prepare the tablet of the present invention. This tablet was orally administered to beagles, blood was collected, and the plasma glucose concentration was determined under the same conditions as described above. D and Cmin were calculated from changes in the blood glucose concentration that was obtained by the same method as used for the control.

Example 7

First, 500 U (17.8 mg) insulin, 125 mg E-SD, and 57.2 mg DL-malic acid were mixed and a core tablet was obtained by molding under a tableting pressure of 40 kg/cm$^2$ using an oil press. Then 100 mg polyethylene oxide (brand name Polyox-WSR303, Union Carbide Co., Ltd.; PEO hereafter) and 200 mg PEG6000 were mixed to prepare a PEO/PEG mixed powder. Half was added to a mortar for tableting and then the core tablet was placed in the center of the mortar. Then the other half of the PEO/PEG mixed powder was added to the mortar and the tablet of the present invention with an outer layer was prepared by molding under a tableting pressure of 40 kg/cm$^2$ using an oil press. This tablet with a core was orally administered to beagles, blood was collected, and the plasma glucose concentration was determined under the same conditions as described above. D and Cmin were calculated from the changes in the plasma glucose concentration that was obtained by the same method as in Control 5.

[Results and Discussion]

The results that were obtained are shown in Table 7.

TABLE 7

|  | D (% of initial*h) | Cmin (% of initial) |
|---|---|---|
| Control | −2.1 ± 9.8 | 94.0 ± 4.7 |
| Example 6 | 34.6 ± 62.1 | 88.3 ± 6.0 |
| Example 7 | 53.3 ± 31.0 | 79.4 ± 9.0 |

(mean ± SD, n = 3)

Almost no reduction in the blood glucose level was seen up to 8 hours after administration with singular administration of insulin. On the other hand, either an increase in the D value or a reduction in the Cmin value was seen in Examples 6 and 7, and there was a tendency toward a reduction in the glucose level with oral administration of E-SD together with insulin. Moreover, according to the results of Examples 6 and 7, dissolution and dispersion of E-SD in the stomach can be prevented by tablets whose active ingredient dissolves somewhere between the small intestines and the large intestines (Example 7) rather than tablets that are disintegrated in the stomach (Example 6) and therefore, a tendency toward augmentation of the reduction in the blood glucose level was seen. These results indicate that the effect of insulin by oral administration is improved when aminoalkyl methacrylate copolymer E to which acid has been added is used.

INDUSTRIAL APPLICABILITY

The aminoalkyl methacrylate copolymer E used as an active ingredient in the present invention is useful as an agent for inhibiting decomposition of a biologically active peptide by a digestive enzyme. Moreover, the aminoalkyl methacrylate copolymer E used as an active ingredient of the present invention is useful as an agent for reducing viscosity of the gastrointestinal mucosa and/or mucous layers distributed over this mucosa. The aminoalkyl methacrylate copolymer E used as an active ingredient in the present invention has the ability to improve permeability of a biologically active peptide in the gastrointestinal mucosa and/or mucous layers distributed over the mucosa and therefore, is useful as an excellent agent for improving oral absorption of a biologically active peptide. The pharmaceutical composition of the present invention can realize excellent absorption by oral administration of a biologically active peptide, which had been considered difficult to absorb by oral administration in the past, based on the ability of aminoalkyl methacrylate copolymer E to inhibit decomposition of a biologically active peptide, its ability to reduce viscosity of the gastrointestinal mucosa and/or mucous layers distributed over this mucosa, and its ability to improve permeability of a biologically active peptide in the mucous layers. In addition, the pharmaceutical composition of the present invention is useful as one that presents pharmaceutical preparation technology appropriate for many uses, such as several types of a biologically active peptide, including insulin, calcitonin, vasopressin, and the like.

The invention claimed is:

1. A method for inhibiting decomposition of a biologically active peptide, said method comprising orally administering an aminoalkyl methacrylate copolymer E, which is a copolymer of methyl methacrylate, butyl methacrylate, and dimethylaminoethyl methacrylate, to prevent decomposition of said biologically active peptide by a digestive enzyme, wherein said aminoalkyl methacrylate copolymer E is used in the presence of an acidic substance, said acidic substance being an inorganic acid or an organic acid; wherein the amount of the acidic substance added is 0.005-50 parts by weight per 1 part by weight of aminoalkyl methacrylate copolymer E; and wherein the active peptide is formed into a member selected from the group consisting of a tablet, a pill, a liquid, a suspension, an emulsion, and a capsule.

2. The method according to claim 1, wherein the digestive enzyme is trypsin or elastase.

3. The method according to claim 1, wherein the amount of aminoalkyl methacrylate copolymer E is 0.1 part by weight or more per one part by weight of said biologically active peptide.

4. The method according to claim 1, wherein the amount of the acidic substance added is the amount to neutralize 15% to 50% of the basic groups of aminoalkyl methacrylate copolymer E.

5. The method according to claim 1, wherein said biologically active peptide and aminoalkyl methacrylate copolymer E are comprised in a pharmaceutical composition.

6. The method according to claim 5, wherein the pharmaceutical composition comprises said biologically active peptide, aminoalkyl methacrylate copolymer E, and an acidic substance, wherein said three components are brought together and at least said polymer and said acidic substance are uniformly mixed.

7. The method according to claim 6, wherein said biologically active peptide, aminoalkyl methacrylate copolymer E, and said acidic substance are uniformly mixed.

8. The method according to claim 6 or 7, wherein the amount of aminoalkyl methacrylate copolymer E added is 0.1 part by weight or more per one part by weight of said biologically active peptide.

9. The method according to claim 6 or 7, wherein the amount of acidic substance added is the amount to neutralize 10% to 40% of the basic groups of aminoalkyl methacrylate copolymer E.

10. The method according to claim 6 or 7, wherein aminoalkyl methacrylate copolymer E and the acidic substance are granulated.

11. The method according to claim 6 or 7, wherein the pharmaceutical composition is obtained by dissolving and/or dissolving aminoalkyl methacrylate copolymer E and acidic substance in a pharmaceutically acceptable solvent and spray drying to produce a spray-dried substance, or freeze-drying to produce a freeze-dried substance after dissolution.

12. The method according to claim 11, wherein aminoalkyl methacrylate copolymer E and the acidic substance are dissolved and/or suspended in a pharmaceutically acceptable solvent.

13. The method according to claim 6 or 7, wherein the form of the pharmaceutical preparation is one or two or more selected from the group consisting of a tablet, a capsule, and a liquid.

14. The method according to claim 6 or 7, wherein the biologically active peptide is one of that is decomposed by a digestive enzyme and/or one of that is difficult to absorb.

15. The method according to claim 14, wherein the biologically active peptide is calcitonin, insulin, or vasopressin.

* * * * *